US006666907B1

(12) United States Patent
Manginell et al.

(10) Patent No.: US 6,666,907 B1
(45) Date of Patent: Dec. 23, 2003

(54) TEMPERATURE PROGRAMMABLE MICROFABRICATED GAS CHROMATOGRAPHY COLUMN

(75) Inventors: Ronald P. Manginell, Albuquerque, NM (US); Gregory C. Frye-Mason, Cedar Crest, NM (US)

(73) Assignee: Sandia Corporation, Albuquerque, NM (US)

( * ) Notice: Subject to any disclaimer, the term of this patent is extended or adjusted under 35 U.S.C. 154(b) by 3 days.

(21) Appl. No.: 10/061,383

(22) Filed: Jan. 31, 2002

(51) Int. Cl.⁷ ............................................. B01D 15/08
(52) U.S. Cl. ..................... 95/87; 73/23.36; 73/23.39; 96/102; 96/105; 96/107
(58) Field of Search ...................... 73/23.35, 23.36, 73/23.39, 23.41; 95/82, 87; 96/101–103, 105

(56) References Cited

U.S. PATENT DOCUMENTS

| | | | | |
|---|---|---|---|---|
| 3,449,938 A | * | 6/1969 | Giddings | 73/23 |
| 3,486,298 A | * | 12/1969 | Huebner | 55/67 |
| 3,630,006 A | * | 12/1971 | Sandoval | 55/386 |
| 3,748,833 A | * | 7/1973 | Karas et al. | 55/197 |
| 4,350,586 A | * | 9/1982 | Conlon et al. | 210/149 |
| 4,726,822 A | * | 2/1988 | Cates et al. | 55/267 |
| 4,891,120 A | * | 1/1990 | Sethi et al. | 204/299 R |
| 4,923,486 A | * | 5/1990 | Rubey | 55/67 |
| 4,969,938 A | * | 11/1990 | America | 55/386 |
| 5,005,399 A | * | 4/1991 | Holtzclaw et al. | 73/23.39 |
| 5,028,243 A | * | 7/1991 | Rubey | 55/67 |
| 5,087,275 A | * | 2/1992 | Pribat et al. | 55/386 |
| 5,092,218 A | * | 3/1992 | Fine et al. | 55/67 X |
| 5,135,549 A | * | 8/1992 | Phillips et al. | 55/67 |
| 5,376,252 A | * | 12/1994 | Ekstrom et al. | 204/299 R |
| 5,376,277 A | * | 12/1994 | Cortes et al. | 210/659 |
| 5,522,918 A | * | 6/1996 | Shiramizu | 95/87 |
| 5,544,276 A | * | 8/1996 | Loux et al. | 392/480 |
| 5,658,413 A | * | 8/1997 | Kaltenbach et al. | 156/272.8 |
| 5,720,798 A | * | 2/1998 | Nickerson et al. | 96/102 |
| 5,779,765 A | * | 7/1998 | Grob et al. | 95/83 |
| 5,792,943 A | * | 8/1998 | Craig | 73/61.52 |
| 5,997,708 A | * | 12/1999 | Craig | 204/601 |
| 6,054,683 A | * | 4/2000 | Bremer et al. | 219/388 |
| 6,068,684 A | | 5/2000 | Overton | 96/104 |
| 6,068,780 A | * | 5/2000 | Yu | 216/10 |
| 6,171,378 B1 | | 1/2001 | Manginell et al. | 96/143 |
| 6,209,386 B1 | * | 4/2001 | Mustacich et al. | 73/23.39 |
| 6,223,584 B1 | * | 5/2001 | Mustacich et al. | 73/23.41 |
| 6,296,685 B1 | * | 10/2001 | Cammann et al. | 95/45 |
| 6,454,840 B1 | * | 9/2002 | Gellert et al. | 96/101 |

OTHER PUBLICATIONS

Mowry, et al., "Micropyrolyzer for Chemical Analysis of Liquid and Solid Samples," Patent Application No. 10/035,537, filed Oct. 23, 2001.

Kottenstette, et al., "Microfabricated Packed Chromatographic Column," Provisional Patent Application No. 60/336,546, filed Nov. 2, 2001.

(List continued on next page.)

Primary Examiner—Robert H. Spitzer
(74) Attorney, Agent, or Firm—Kevin W. Bieg

(57) ABSTRACT

A temperature programmable microfabricated gas chromatography column enables more efficient chemical separation of chemical analytes in a gas mixture by the integration of a resistive heating element and temperature sensing on the microfabricated column. Additionally, means are provided to thermally isolate the heated column from their surroundings. The small heat capacity and thermal isolation of the microfabricated column improves the thermal time response and power consumption, both important factors for portable microanalytical systems.

31 Claims, 5 Drawing Sheets

OTHER PUBLICATIONS

Matzke, et al., "Microfabricated silicon gas chromatographic micro–channels: fabrication and performance," *Proceedings of SPIE, Micromachining and Microfabrication Process Technology IV, 3511*, 262 (1998).

Menz, et al., *Microsystems Technology*, Wiley–VCH, Weinheim, pp. 265–268 (2001).

Frye–Mason, et al., "Hand–Held Miniature Chemical Analysis System (uChemLab) for Detection of Trace Concentrations of Gas Phase Analytes," *Micro Total Analysis Systems 2000*, 229 (2000).

Morgan, et al., "Rapid Identification of Bacteria with Miniaturized Pyrolysis/GC Analysis," *Proceedings of SPIE, Advanced Environmental and Chemical Sensing Technology, 4205*, 199 (2001).

Frye–Mason, et al., "Expanding the Capabilities and Applications of Gas Phase Miniature Chemical Analysis Systems ($\mu$ChemLab™," *Micro Total Analysis Systems 2001*, 658 (2001).

* cited by examiner

TEMPERATURE PROGRAMMABLE MICROFABRICATED GAS CHROMATOGRAPHY COLUMN

STATEMENT OF GOVERNMENT INTEREST

This invention was made with Government support under contract no. DE-AC04-94AL85000 awarded by the U.S. Department of Energy to Sandia Corporation. The Government has certain rights in the invention.

BACKGROUND OF THE INVENTION

The present invention relates generally to chemical separations in microanalytical systems and, more particularly, to temperature programming of a microfabricated gas chromatography column for efficient separation of gas-phase analytes.

Portable, handheld microanalytical systems, which have been termed "chemical laboratories on a chip," are being developed to enable the rapid and sensitive detection of particular chemicals, including pollutants, high explosives, and chemical warfare agents. These microanalytical systems should provide a high chemical selectivity to discriminate against potential background interferents and the ability to perform the chemical analysis on a short time scale. In addition, low electrical power consumption is needed for prolonged field use. See, e.g., Frye-Mason et al., "Hand-Held Miniature Chemical Analysis System ($\mu$ChemLab) for Detection of Trace Concentrations of Gas Phase Analytes," *Micro Total Analysis Systems* 2000, 229 (2000).

Current gas-phase microanalytical systems are based on gas chromatography (GC). Gas chromatography relies upon the chemical equilibria of analytes between a mobile phase and a stationary phase in a GC column to bring about a temporal separation of analytes in a gas mixture. Chemical equilibria and, therefore, column retention times are strongly influenced by column temperature. Thus, column temperature must be precisely controlled to obtain accurate separations.

The goal of a GC analysis is normally to obtain a separation with the required accuracy in the minimum time. Isothermal operation of the GC column can have drawbacks for achieving this goal with certain gas mixtures. If the selected isothermal temperature is too low, early-eluted peaks will be closely spaced whereas more strongly retained analytes will have broad and low-lying peaks and consequent poor detectability. Conversely, the more strongly retained analytes will elute faster at a higher isothermal column temperature, but at the expense of poorer separation and loss of resolution for the early eluting analytes.

This general elution problem may be solved by temperature programming of the column. With temperature programming, analysis time can be reduced and the overall detectability of components can be improved. For example, for a given column it is possible to analyze gas mixtures with a broader volatility range in a shorter analysis time with temperature programming. For most analytes, the baseline resolution and peak widths are also improved. In general, temperature programming can comprise a series of changes in the column temperature that can include isothermal and controlled temperature rise segments. As an example of temperature programming, consider temperature ramping. Temperature ramping comprises monotonically increasing the temperature as the gas mixture is passed through the column. Higher volatility analytes in the mixture, which without temperature ramping pass through the column the earliest, still are the first to arrive at the column exit. Temperature ramping only tends to modestly improve the peak widths of these early eluting analytes and enhances baseline resolution somewhat. This is mainly due to the fact that these faster eluting analytes pass through the column before the initial temperature is appreciably increased. On the other hand, less volatile analytes, which in the absence of ramping tend to elute slowly with relatively broad and low-lying peaks, elute more quickly with temperature ramping and are generally improved from the standpoint of baseline resolution and peak width. As a result, analysis time can be improved relative to a low temperature, isothermal elution while retaining resolution.

In conventional chromatography, an oven enclosing the GC column is used to effect the temperature program. This process is energy intensive, requiring hundreds of watts of power, and is capable of providing only modest ramp rates of about 25° C./min. These characteristics are adequate for laboratory applications where power is not that limited, and long, 30 meter columns can be used to separate difficult mixtures without the need for faster ramp rates. However, for portable applications, this level of power consumption is unacceptable. Further, given the necessarily shorter length of portable GC columns relative to laboratory instruments, more rapid temperature ramping can compensate for the loss of resolution due to fewer theoretical plates in the portable GC column. Thus, there exists a need for temperature programming of microfabricated GC columns suitable for a portable, energy-efficient microanalytical system.

The present invention solves the need for a temperature programmable microfabricated GC column through the integration of a resistive heating element and temperature sensing on microfabricated GC column. Additionally, means are provided to thermally isolate the heated-column from its surroundings. The thermal isolation reduces power losses from the heated zone and reduces column heat capacity, thereby improving the thermal time response and power consumption, both important factors for portable GC applications. The present invention permits rapid, low-power and sensitive temperature programming of the microfabricated GC column and temperature ramp rates that are an order of magnitude faster than conventional GC columns, thereby enabling more efficient chemical separations.

SUMMARY OF THE INVENTION

The present invention comprises a temperature programmable microfabricated gas chromatography column comprising a substrate, a channel etched in the substrate to separate chemical analytes in a gas mixture, at least one lid disposed on a channel-side of the substrate to seal the channel, and at least one resistive heating element disposed on a least one surface of the substrate to heat the column during the separation. The temperature programmable microfabricated gas chromatography column can further comprise a control board for electrical control of the resistive heating element and fluidic control of the column, means for electrically connecting the control board to the resistive heating element, means for fluidically connecting the control board to the channel, and means for thermal isolation of control board from the substrate.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 5A shows the chromatogram of an isothermal low temperature elution. FIG. 5B shows the chromatogram of a temperature ramping elution. FIG. 5C shows the chromatogram of an isothermal high temperature elution.

DETAILED DESCRIPTION OF THE INVENTION

Figure 1:
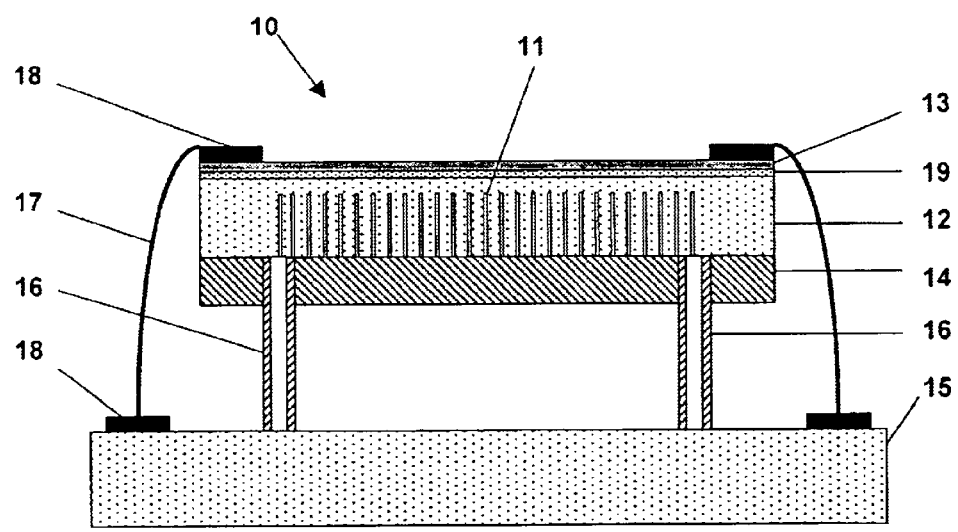
FIG. 1 shows a schematic side-view of a temperature programmable microfabricated GC column.

The present invention comprises a temperature programmable microfabricated GC column. In FIG. 1 is shown a schematic illustration of the temperature programmable microfabricated CG column 10, comprising a channel 11 formed in a substrate 12, a lid 14 to seal the channel 11, and a resistive heating element 13 disposed on a surface of the substrate 12 to heat the column 10 during the separation of chemical analytes in a gas mixture. The column 10 can be mounted on a fluidic/electronic control board 15 that can be separated from the substrate by tubes 16 for thermal isolation and fluid coupling to the channel 11. The electrical controller on the control board 15 can be electrically connected to the resistive heating element 13 by wires 17 bonded to pads 18. This configuration permits rapid temperature ramping of the column 10 at a low power suitable for portable microanalytical applications.

Preferably, the temperature programmable microfabricated GC column 10 can be fabricated by depositing the resistive heating element 13 on a surface of the substrate 12, etching the channel 11 in the side of the substrate 12 opposite to the resistive heater 13, and bonding the lid 14 to the etched side of the substrate 12 to seal the channel 11. Inlet and outlet tubes 16 can be attached through the lid 14 to the channel-side of the substrate 12 and to the control board 15. The channel 11 can be coated with a stationary phase. Electrical wires 17 can then be bonded to pads 18 on the resistive heating element 13 and the substrate 12.

The substrate 12 can comprise a substantially planar sheet or plate of silicon, glass, ceramic, or other suitable GC column material. For example, the substrate 12 can be a single crystal silicon wafer.

Depending on the resistive heating element and substrate materials, a dielectric thin film layer 19 can first be deposited on the substrate 12 to electrically isolate the resistive heating element 13 from the substrate 12. For example, the insulating layer 19 can be a 0.5 $\mu$m-thick layer of silicon nitride deposited by chemical vapor deposition on a silicon wafer 12. The heating element 13 can comprise a resistive material, such as a refractory metal or lightly doped semiconductor material. The resistive heating element 13 can be a layer deposited by thin-film techniques, such as physical vapor deposition, or by thick-film techniques, such as screen-printing. For example, the resistive heating element 13 can comprise a less than 0.1 $\mu$m thick layer of platinum on a thin (e.g., 10–15 nm thickness) titanium adhesion layer. Alternatively, the resistive heating element 13 can comprise a patterned layer having a circuitous or serpentine pattern, multiple heating elements, or a layer of variable cross-section or resistivity to provide for a uniform or tailored temperature over the area of the channel 11. The bond pads 18 can be gold of about 1 $\mu$m thickness.

The channel 11 for the GC column 10 can be formed in the substrate 12 by a variety of processes such as those described by Matzke et al., "Microfabricated Silicon Gas Chromatographic MicroChannels: Fabrication and Performance," *Proceedings of SPIE, Micromachining and Microfabrication Process Technology IV*, 3511, 262 (1998) and in U.S. Pat. No. 6,068,684 to Overton, which are incorporated herein by reference. For example, the channel 11 can be a deep high-aspect-ratio channel formed in the side of the substrate 12 by anisotropic wet etching or plasma etching. The high-aspect-ratio cross-section enables close packing of a spiral or serpentine channel 11 to achieve a desired column length. A typical microfabricated silicon-based GC column 10 comprises a 1-meter spiral channel 11 formed on a 1.0–1.5 cm$^2$ area of a silicon wafer 12. A typical channel 11 can have a cross-section that is 40–100 $\mu$m wide by 300–400 $\mu$m deep. The channel cross-section can be varied along the channel length to optimize the separation efficiency along the channel 11 and to enable operation over a wider temperature range.

Preferably, the channel 11 can be formed in the substrate 12 opposite the resistive heating element 13 and a lid 14 can be attached to the channel-side of the substrate 12 to seal the open channel 11. The lid 14 is preferably a thermally insulating material and thin to minimize the heat capacity of the column 10. The lid 14 can be made from a thin sheet of a material such as glass or polymer. For example, the lid 14 can be a machined Pyrex lid that is anodically bonded to the deep-etched silicon wafer 12. The Pyrex lid 14 can be less than 1 mm in thickness, and preferably about 250 $\mu$m or less in thickness. Inlet and outlet holes can be formed in the lid 14, for example, by grinding. Following bonding of the lid 14 to the substrate 12, the channel 11 can be cleaned, for example, with a sulfuric acid/hydrogen peroxide cleaner. Tubes 16 can be capillary tubes that are attached, for example with epoxy, to the inlet and outlet holes in the lid 14 to fluidically connect the channel 11 to the control board 15.

Alternatively, the resistive heating element 13 can be disposed on the channel-side surface of the substrate 12 by depositing a layer of the resistive material on the exposed surface of the lid 14. An additional resistive heating element (not shown) can be disposed on the side of the substrate 12 opposite the first resistive heater 13 to further increase the column heating rate and heating uniformity. Furthermore, the at least one resistive material layer can be deposited on the surface of the substrate 12 or lid 14 after the lid 14 is bonded to the substrate 12.

Alternatively, the channel 11 can be etched completely through the substrate 12 and sealed by a top lid (not shown) bonded to the top surface and the bottom lid 14 bonded to the bottom surface of the substrate 12. At least one resistive heating element 13 can be disposed on at least one surface of the substrate 12 by depositing resistive material layers on the exposed surfaces of one or both of the lids.

The inside surfaces of the channel 11 can be coated with a stationary phase material to enhance the separation of the chemical analytes of interest in the gas mixture to be analyzed. The stationary phase material can be a polymer having a specific chemical group with the proper physico-chemical interaction to cause separation of the analytes. The channel 11 can be coated with the stationary phase material by pushing a plug of the material through the channel 11 or by filling the channel 11 with a solvent containing the stationary phase material and then applying a vacuum to the end of the channel 11 to dry the solvent out of the channel 11. The stationary phase can also be applied by gas or liquid phase deposition into the channel 11 prior to bonding the lid 14 to the substrate 12. Instead of using a stationary phase material to coat the surfaces of the channel 11, the channel can alternatively be filled with a porous packing material to make a microfabricated packed GC column.

The control board 15 can be a printed wiring board (PWB) or a ceramic substrate, such as a low temperature co-fired ceramic (LTCC), that can be connected fluidically to the channel 11 by the tubes 16. The control board 15 can be electrically connected to the heated column 10 by wirebonding or soldering of fine wires 17 to bond pads 18 on the control board 15 and the resistive heating element 13. The resulting microfabricated GC column 10 provides advantages compared to conventional GC columns in terms of cost, system size, and power required to heat and temperature control the column.

Through the known temperature coefficient of resistance (TCR) of the resistive heating element material, the temperature of the column 10 can be measured. In this mode, the resistive heating element 13 acts as both heater and temperature sensor. Alternatively, a temperature sensor 20 can be fabricated separate from the resistive heating element 13. Because microfabrication is used throughout, various types of temperature sensors 20 can be used to sense temperature, including diodes, thin film thermistors, thermocouples, and thermopiles. See e.g., W. Menz, J. Mohr, and O. Paul, *Microsystems Technology*, Wiley-VCH, Weinheim (2001).

Figure 2:
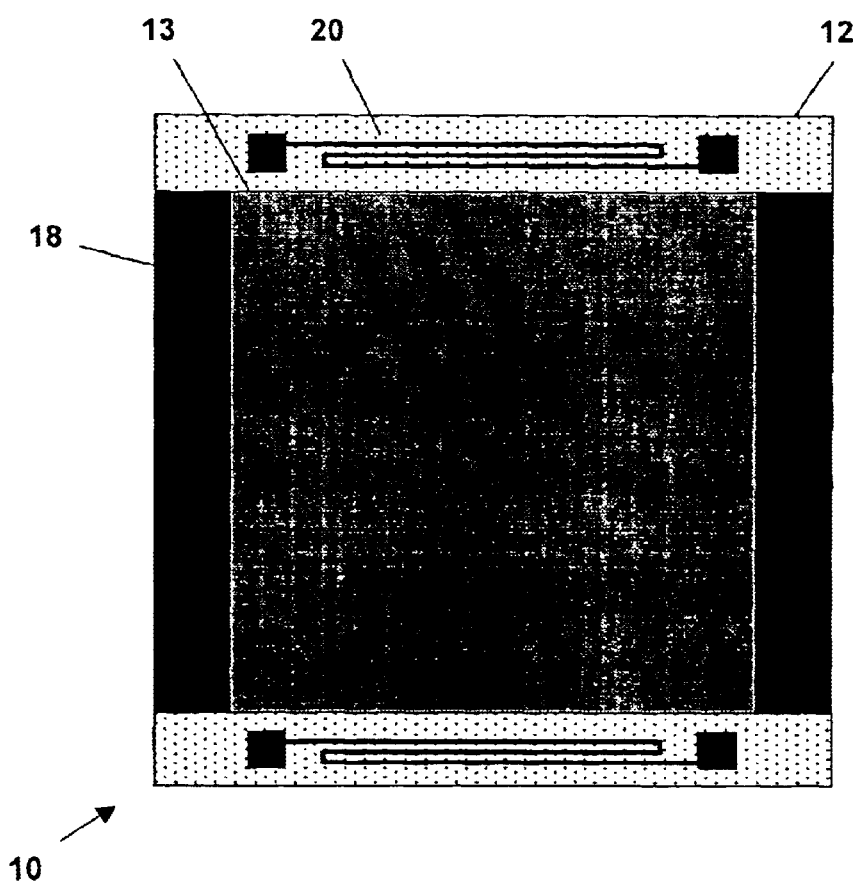
FIG. 2 shows a schematic top-view of a GC column showing an integral thin-film resistive heating element with separate temperature sensors.

FIG. 2 shows a top-view of a resistive heating element 13 and separate temperature sensors 20, comprising a thermistor material deposited in a serpentine pattern on the upper surface of the substrate 12. By placing the resistive heating element 13 and temperature sensor 20 in intimate contact with the surface of the channel-containing substrate 12 (by either hybrid or monolithic methods), fine temperature control and time response can be accomplished.

Figure 3:
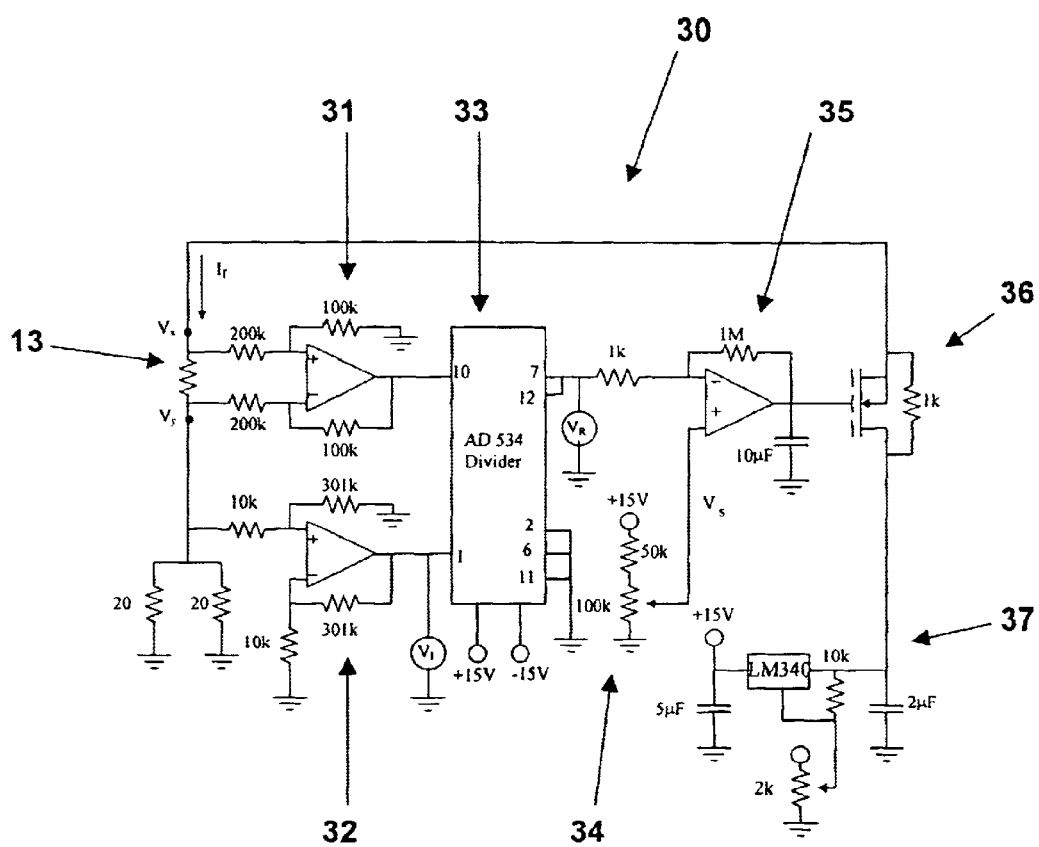
FIG. 3 shows a circuit diagram for control of the resistive heating element.

A variety of electronic control circuits can be used to control the temperature of the GC column 10. FIG. 3 shows a control circuit 30 that can be used for operation of the column 10 when the resistive heating element 13 is used to both heat and sense the column temperature. Since the temperature coefficient of resistance of materials is well known, the temperature is equivalent to the resistance of the resistive heating element 13. The feedback control circuit 30 measures the power (or current) necessary to maintain the resistive heating element 13 at the programmed temperature. A first operational amplifier 31 measures the voltage across the resistive heating element 13. A second operational amplifier 32 produces a voltage $V_f$ that is proportional to the current $I_f$ through the resistive heating element 13. Therefore, the output voltage $V_R$ of divider 33 (e.g., an Analog Devices AD 534 chip) is proportional to the resistance of the resistive heating element 13. Using differential amplifier 35, $V_R$ can be compared to a programmed voltage $V_S$ that can be provided from a voltage divider 34 or from an external source such as a D-to-A converter. The programmed voltage $V_S$ determines the desired resistance (i.e., temperature) of the resistive heating element 13. The comparator output of the differential amplifier 35 controls the gate of transistor 36 that feeds back to the resistive heating element 13 to maintain the desired temperature of the GC column 10. The larger the difference between the divider voltage $V_R$ and the programmed voltage $V_S$, the greater the feedback current $I_f$ that is switched from power supply 37 to the resistive heating element 13. Other circuits of the type known in the electronic control art can be used to control the resistive heating element 13 with separate temperature sensor 20.

Table I shows heating rates and power requirements for an exemplary temperature programmable microfabricated GC column 10, comprising an 86 cm long×100 μm wide×400 μm deep channel 11 etched in a 1.3 cm.×1.3 cm.×525 μm thick silicon wafer 12. The resistive heating element 13 comprised a 30 nm thickness platinum layer deposited on a 10 nm thickness titanium adhesion layer deposited on the surface of the silicon wafer 12 opposite the channel 11. The channel 11 was sealed by a 500 μm thick Pyrex lid 14 on the channel side of the substrate 12, opposite the resistive heating element 13. The column temperature was monitored by a thermistor-type temperature sensor 20 mounted on the silicon wafer 12 and connected to an electronic control circuit.

TABLE I

| Heater Voltage | Cold Temp (° C.) | Hot Temp (° C.) | Time (sec.) | Heater Power (W) | Heating Rate (° C./sec.) |
|---|---|---|---|---|---|
| 4 | 32 | 50 | 27.4 | 0.42 | 0.65 |
| 7.9 | 23 | 100 | 31 | 1.7 | 2.4 |
| 11.8 | 27 | 120 | 14.2 | 3.8 | 6.5 |
| 15.7 | 29 | 120 | 7 | 6.8 | 13.0 |
| 19.7 | 38 | 120 | 4.5 | 10.4 | 20.1 |

Because the resistive heating element 13 is integrated in a low heat capacity column 10 that is thermally isolated from the control board 15, heating rates of 0.65° C./sec with 0.42 W of heater power, and 20° C./sec with 10.4 W, can be achieved. These heating rates are about an order of magnitude faster, with at least an order of magnitude less power consumption, than are typical of conventional heated GC columns.

Figure 4:
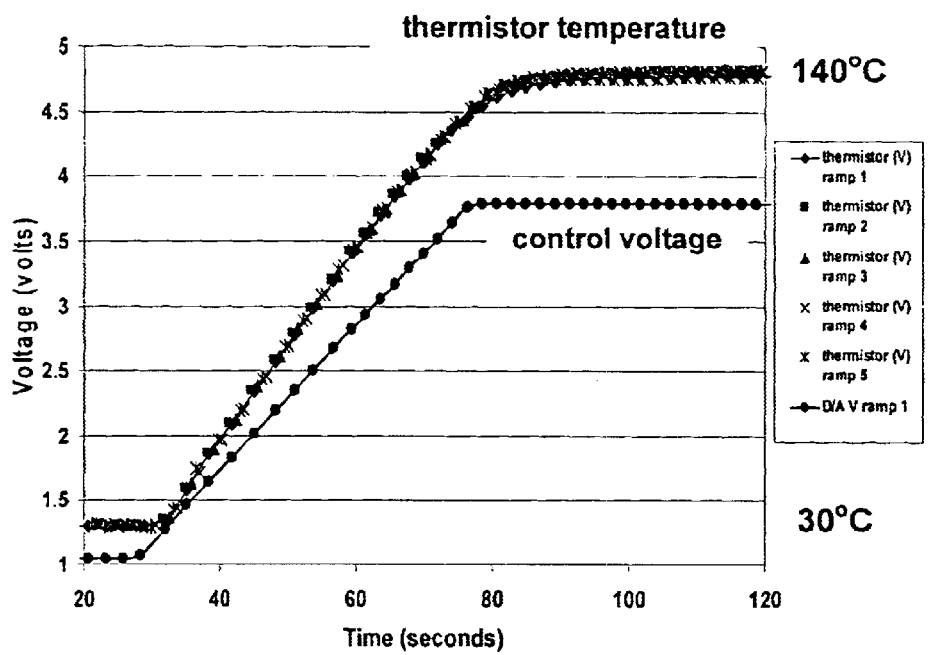
FIG. 4 shows a graph of reproducible temperature ramps as a function of programmed control voltage.

To obtain an accurate analysis, a consistent retention time should be obtained for a particular analyte and column condition. In particular, the control circuit 30 should provide a reproducible temperature ramp of the column 10. FIG. 4 shows a graph of the column temperature, as measured by a thermistor-type temperature sensor 20, for five separate temperature tests with the same programmed control voltage ramp. A monotonic temperature ramp was reproduced accurately for each test, enabling consistent analyte separations. This reproducibility is easily achieved with the microfabricated GC column 10 of the present invention because of the good thermal contact between the substrate 12 and the resistive heating element 13.

In a typical GC analysis, a plug of the gas mixture to be analyzed is injected into the channel 11 via inlet tube 16. For example, the gaseous plug can be generated by the rapid release of sorbed chemical species from a chemical preconcentrator, as disclosed in U.S. Pat. No. 6,171,378 to Manginell et al., or by the rapid vaporization of a liquid sample or pyrolyzation of a solid sample by a micropyrolyzer, as disclosed in U.S. patent application Ser. No. 10/035,537 to Mowry, et al., both of which are incorporated herein by reference. The column 10 is then heated by the resistive heating element 13 according to a prescribed temperature program. The analytes in the injected gas mixture are thereby separated with their retention time being dependent on the physico-chemical properties of the channel 11 and the temperature program. The separated analytes can then be removed from the channel 11 through an outlet tube 16 and passed over a detector that measures some property of the gas, such as thermal conductivity. A chromatogram, showing detector response versus retention time, can thereby be recorded.

Figures 5A, 5B, 5C:
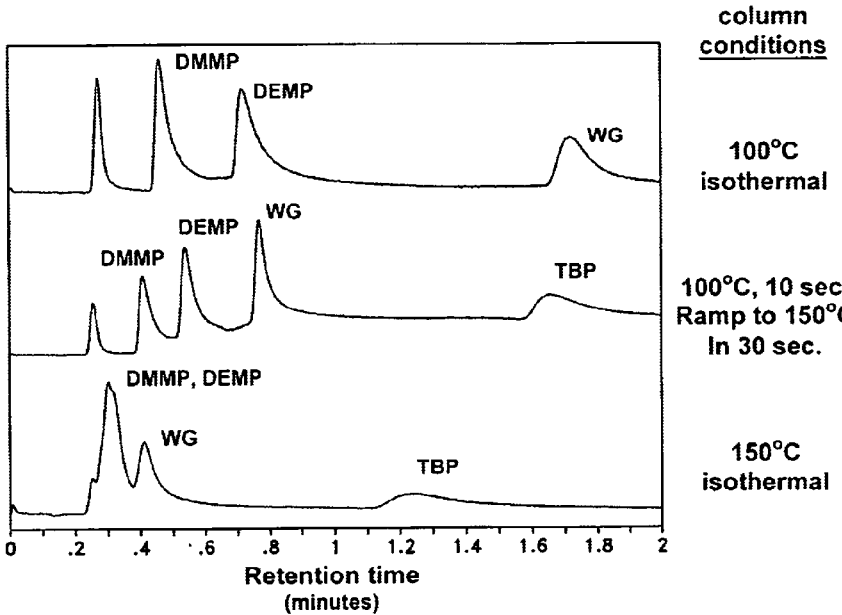
FIGS. 5A–5C show chromatograms of a mixture of chemical analytes having a wide volatility range.

FIGS. 5A–5C show chromatograms of a mixture of chemical analytes having a wide volatility range obtained with both isothermal and temperature-programmed columns. The chromatograms were obtained with a GC column 10 similar to that used to obtain the data in Table 1 and a flame ionization detector was used to detect the separated analytes.

As shown in FIG. 5C, an isothermal column may require an operating temperature of as high as 150° C. to obtain an elution of the stronger retained analyte, tributyl phosphate (TBP) in a reasonable retention time. However, with this high isothermal column temperature, the peaks of the early eluting analytes, dimethyl methyl phosphonate (DMMP), diethyl methyl phosphonate (DEMP), and wintergreen (WG), display poor separation. Conversely, as shown in FIG. 5A, at a low isothermal column temperature of 100° C., the higher volatility analytes, DMMP and DEMP, show good separation, but the peaks of the lower volatility analytes are broadened and poorly resolved above the baseline and the TBP does not elute during the two-minute analysis time. The chromatogram in FIG. 5B shows the separation achieved with a temperature program providing a 10 second segment at a column temperature of 100° C., followed by a 30 second temperature ramp to 150° C. (i.e., a heating rate of 1.67° C./sec or 100° C./min). The initial low temperature segment provides good separation of the higher volatility analytes and the temperature ramp segment provides good detectability of the lower volatility analytes.

These data show that temperature programming of a microfabricated GC column 10 having an integral resistive heating element 13 can significantly improve separation of some gas mixtures. Furthermore, temperature programming compensates for the limited number of plates available in short-column microfabricated GCs, as compared with long-column conventional laboratory GCs. This microfabricated GC column enables a low-power, efficient portable microanalytical system.

The embodiments of the present invention have been described as a temperature programmable microfabricated gas chromatography column. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method for separating a plurality of chemical analytes in a gas mixture, comprising:

injecting the gas mixture into a temperature programmable microfabricated gas chromatography column, the column comprising:

a substrate having a first surface and a second surface;

a continuous channel formed in at least one surface of the substrate to separate the plurality of chemical analytes between an inlet end and an outlet end of the channel;

at least one lid bonded to the at least one surface of the substrate having the channel formed therein to seal the channel;

at least one resistive heating element deposited on at least one surface of the substrate to heat the column during the separation of the plurality of chemical analytes;

a control board for electrical control of the at least one resistive heating element and fluidic control of the channel;

means for electrically connecting the control board to the at least one resistive heating element to heat the column; and an inlet tube fluidically connecting the control board to the inlet end of the channel for injection of the gas mixture therein and an outlet tube fluidically connecting the control board to the outlet end of the channel for removal of the chemical analytes therefrom, and wherein the inlet tube and the outlet tube thermally isolate the control board from the substrate; and heating the column according to a prescribed temperature program to separate the plurality of chemical analytes in the gas mixture.

2. The method of claim 1, wherein the prescribed temperature program comprises a temperature ramp.

3. The method of claim 2, wherein the temperature ramp is greater than 1° C./sec.

4. The method of claim 2, wherein the temperature ramp is greater than 10° C./sec.

5. The method of claim 2, wherein the temperature ramp is greater than 20° C./sec.

6. The method of claim 1, wherein the step of injecting the gas mixture comprises releasing the plurality of chemical analytes from a sorptive material.

7. The method of claim 6, wherein the releasing the plurality of chemical analytes comprises heating the sorptive material in a chemical preconcentrator.

8. The method of claim 1, wherein the step of injecting the gas mixture comprises vaporizing the plurality of chemical analytes from a liquid sample.

9. The method of claim 8, wherein the vaporizing the plurality of chemical analytes comprises heating the liquid sample in a micropyrolyzer.

10. The method of claim 1, wherein the step of injecting the gas mixture comprises pyrolyzing the plurality of chemical analytes from a solid sample.

11. The method of claim 10, wherein the pyrolyzing the plurality of chemical analytes comprises heating the solid sample in a micropyrolyzer.

12. A temperature programmable microfabricated gas chromatography column for separation of a plurality of chemical analytes in a gas mixture, comprising:

a substrate having a first surface and a second surface;

a continuous channel formed in at least one surface of the substrate to separate the plurality of chemical analytes between an inlet end and an outlet end of the channel;

at least one lid bonded to the at least one surface of the substrate having the channel formed therein to seal the channel; and at least one resistive heating element deposited on at least one surface of the substrate to heat the column during the separation of the plurality of chemical analytes.

13. The temperature programmable microfabricated gas chromatography column of claim 12, further comprising:

a control board for electrical control of the at least one resistive heating element and fluidic control of the channel;

means for electrically connecting the control board to the at least one resistive heating element to heat the column;

an inlet tube fluidically connecting the control board to the inlet end of the channel for injection of the gas mixture therein and an outlet tube fluidically connecting the control board to the outlet end of the channel for removal of the chemical analytes therefrom, and wherein the inlet tube and the outlet tube thermally isolate the control board from the substrate.

14. The temperature programmable microfabricated gas chromatography column of claim 13, wherein the column is heated according to a prescribed temperature program.

15. The temperature programmable microfabricated gas chromatography column of claim 14, wherein the prescribed temperature program comprises a temperature ramp of greater than 1° C./sec.

16. The temperature programmable microfabricated gas chromatography column of claim 14, wherein the prescribed temperature program comprises a temperature ramp of greater than 10° C./sec.

17. The temperature programmable microfabricated gas chromatography column of claim 14, wherein the prescribed temperature program comprises a temperature ramp of greater than 20° C./sec.

18. The temperature programmable microfabricated gas chromatography column of claim 12, wherein the channel is formed in the first surface of the substrate and the at least one lid comprises a first lid having a first surface and a second surface and wherein the first surface of the first lid is bonded to the first surface of the substrate.

19. The temperature programmable microfabricated gas chromatography column of claim 18, wherein the at least one resistive heating element comprises a layer of resistive material deposited on the second surface of the substrate.

20. The temperature programmable microfabricated gas chromatography column of claim 18, wherein the at least one resistive heating element comprises a layer of resistive material deposited on the second surface of the first lid.

21. The temperature programmable microfabricated gas chromatography column of claim 18, wherein the at least one resistive heating element further comprises a layer of resistive material deposited on the second surface of the first lid.

22. The temperature programmable microfabricated gas chromatography column of claim 18, wherein the channel formed in the first surface of the substrate is formed through to the second surface of the substrate and the at least one lid further comprises a second lid having a first surface and a second surface and wherein the first surface of the second lid is bonded to the second surface of the substrate.

23. The temperature programmable microfabricated gas chromatography column of claim 22, wherein the at least one resistive heating element comprises a layer of resistive material deposited on the second surface of the first lid.

24. The temperature programmable microfabricated gas chromatography column of claim 22, wherein the at least one resistive heating element comprises a layer of resistive material deposited on the second surface of the second lid.

25. The temperature programmable microfabricated gas chromatography column of claim 12, further comprising a separate temperature sensor for monitoring the temperature of the gas chromatography column.

26. The temperature programmable microfabricated gas chromatography column of claim 12, wherein the substrate comprises silicon, glass, or ceramic.

27. The temperature programmable microfabricated gas chromatography column of claim 12, wherein the substrate is less than 1 mm in thickness.

28. The temperature programmable microfabricated gas chromatography column of claim 12, wherein the channel width is less than 100 µm.

29. The temperature programmable microfabricated gas chromatography column of claim 12, wherein the at least one resistive heating element comprises at least one layer of resistive material deposited by thin-film or thick-film techniques.

30. The temperature programmable microfabricated gas chromatography column of claim 29, wherein the at least one layer of resistive material is less than 0.1 µm in thickness.

31. The temperature programmable microfabricated gas chromatography column of claim 12, wherein the at least one resistive heating element comprises a refractory metal or a semiconductor material.

* * * * *